United States Patent [19]

Skurkovich

[11] 4,362,155
[45] Dec. 7, 1982

[54] METHOD AND APPARATUS FOR THE TREATMENT OF AUTOIMMUNE AND ALLERGIC DISEASES

[76] Inventor: Simon V. Skurkovich, 261 Congressional La., #709, Rockville, Md. 20852

[21] Appl. No.: 247,205

[22] Filed: Mar. 24, 1981

[51] Int. Cl.³ .............................................. A61M 1/03
[52] U.S. Cl. ................................ 128/214 R; 424/85; 260/112 B
[58] Field of Search ............... 128/214 R; 260/112 B; 424/85

[56] References Cited

U.S. PATENT DOCUMENTS

| | | | |
|---|---|---|---|
| 4,168,261 | 9/1979 | Edy | 260/112 R |
| 4,172,071 | 10/1979 | DeMaeyer | 260/112 R |
| 4,215,688 | 8/1980 | Terman | 128/214 R |
| 4,223,672 | 9/1980 | Terman | 128/214 R |

FOREIGN PATENT DOCUMENTS 1562546  3/1980  United Kingdom ............ 128/214 R

OTHER PUBLICATIONS

Skurkovich and Eremkina, Annals of Allergy, vol. 35, Dec. 1975, pp. 356–360.
Skurkovich et al., Annals of Allergy, vol. 39, Nov. 1977, pp. 344–350.
World Press Review, Nov. 1980, p. 57.
Article "Plasmapheresis Bringing Relief in many Autoimmune Diseases", National Institute of Health, Bethesada, Md.
Nature vol. 247, Feb. 22, 1973, pp. 551–552.
Article "The Probable Role of Interferon in Allergy", Skurkovich & Eremkina, pp. 356–360.
Publication "Lymphocytes' Cytotoxicity", Skurkovich et al., pp. 344–350.
Russian Original, vol. 86, No. 11, Nov., 1978, "Bulletin of Experimental Biology and Medicine", pp. 1473–1476.

*Primary Examiner*—Allan Lieberman
*Assistant Examiner*—P. Short
*Attorney, Agent, or Firm*—Fleit & Jacobson

[57] ABSTRACT

A method and apparatus for the treatment of autoimmune diseases and allergy (hypersensitivity of immediate type). The apparatus ulitizes an absorption system to absorb interferon from whole blood, from plasma, or from plasma with leukocytes. When plasma or plasma with leukocytes is to be treated, the apparatus includes a separator for separating the plasma or plasma with keukocytes from the whole blood. Preferably, the separator also separates lymphocytes from the whole blood. Blood from a patient's circulation system is pumped either directly to an absorbent system or to the separator and then to the absorbent system. The absorbent system includes a sorbent that is designed to selectively absorb interferon from the blood, the plasma, or the plasma with leukocytes. Alternatively, the absorbent system utilizes a combined sorbent having a first component that absorbs interferon and a second component that abosrbs or removes antoantibodies. After absorption, the plasma or plasma with leukocytes regions the formed elements of blood and is returned to the patient's circulation system. With the method of treating autoimmune and allergic diseases, blood is removed from a patient, treated to reduce the level or completely remove interferon, and returned to the patient.

12 Claims, 2 Drawing Figures

METHOD AND APPARATUS FOR THE TREATMENT OF AUTOIMMUNE AND ALLERGIC DISEASES

BACKGROUND OF THE INVENTION

1. Field of the Invention

The present invention relates to the treatment of patients having autoimmune diseases and allergy (hypersensitivity of immediate type). More particularly, the invention provides a method and apparatus for treating such patients by continuously removing interferon from the blood of a patient being treated.

2. Description of the Prior Art

In 1974, an article was published setting forth the hypothesis that one of the mechanisms of development of autoimmune diseases and allergy is hyperproduction of interferon in a patient's body. The article also suggested treating autoimmune diseases and allergy with anti-interferon immunoglobulin (Nature, 247:551, Feb. 22, 1974).

In 1975, interferon was discovered in the blood of patients with autoimmune diseases and allergy, and preliminary positive results were obtained in treatment of autoimmune and allergic diseases with anti-interferon immunoglobulin ("The Probable Role of Interferon in Allergy", *Annals of Allergy*, 35:356, December, 1975).

It is also known from British Pat. No. 1,562,546, entitled "Removing Specific Factors From Blood", to provide an apparatus for continuously acting, externally of the body, on blood circulating from the body. The apparatus described in this reference includes an input tube connected to an artery and an outlet tube connected to a vein of a patient. Blood withdrawn from the patient is passed through a filter membrane which separates plasma from blood cells. The blood cells are returned directly to the patient, while heparin is injected into the plasma. The plasma is then passed through an absorber that removes specific factors from the heparinized plasma. The treated plasma is then mixed with the blood cells and returned to the body. This reference describes the removal of many different specific factors from the blood; however, no mention is made of the possibility of using the apparatus to remove interferon from patents having autoimmune and allergic diseases. Further, no mention is made of the treatment of allergic diseases. There does not appear to be any recognition in the British reference that allergic diseases can be successfully treated with the apparatus.

An article entitled "Preparation of Monospecific Immunoglobulin Against Human Leukocytic Interferon" was published in the April, 1979, *Bulletin Of Experimental Biology And Medicine*. This article was primarily directed to the preparation of anti-interferon immunoglobulin for its further use as a substance for the treatment of various allergic and autoimmune diseases.

U.S. Pat. No. 4,172,071, the contents of which are herein incorporated by reference, describes a process for the purification of preparations having an interferon type activity. The process described in this patent involves contacting a solution containing products with interferon-type activity with an absorbent whose configuration permits the interferon to be retained in a selective manner. The interferon is then separated from the absorbent in a subsequent process.

U.S. Pat. No. 4,168,261, entitled "Method For The Purification Of Interferon Using Porous Glass Beads", the contents of which are herein incorporated by reference, describes the purification of an aqueous interferon solution by subjecting the solution to chromatography on porous glass beads. The interferon is subsequently eluted from the beads at an acidic pH.

Several features distinguish the present invention from U.S. Pat. Nos. 4,172,071 and 4,168,261. For instance, both of the references describe techniques for purifying interferon carried in a supernatant liquid of a tissue culture. Neither of the references is directed to the removal of interferon from blood, plasma, or plasma with leukocytes. Also, neither of the references is directed to the removal of interferon for the purposes of treating autoimmune diseases and allergy (hypersensitivity of the immediate type).

SUMMARY OF THE INVENTION

The present invention provides both a method and an apparatus for the treatment of autoimmune diseases and allergy (hypersensitivity of immediate type).

One embodiment of the invention utilizes an apparatus having a first component or part for taking blood from a patient, a second component or part containing sorbent for removing interferon from the blood, and a third part or component for returning blood having a reduced amount or free from interferon to the patient. Hereinafter, the terminology "free from interferon" will be used to describe blood that has either a reduced level of interferon or is completely free from interferon. The apparatus is a closed system in which all of the parts are in fluid communication. During the treatment of a patient, the process of removing interferon from the blood is continuous. With this embodiment, the apparatus and method absorb interferon from the whole blood of the patient. The whole blood is pumped directly to the absorption system and, after absorption, is returned directly to the patient.

In another embodiment of the invention, a method and apparatus are provided in which interferon is absorbed from plasma. Alternatively, the interferon is absorbed from plasma containing leukocytes. In either of these cases, it is necessary to pass the whole blood through a blood separator before absorption. Such separator can be a filter or a plasma/cell separator of the type manufactured by American Instrument Co. of Silver Spring, Maryland. With this embodiment, blood from the patient is first pumped to the separator. The separator separates the blood into plasma (or plasma with leukocytes) and blood cells. Alternatively, the separator also separates lymphocytes from the blood cells. Then plasma, or plasma with leukocytes, is pumped from the separator to the absorbent system. After absorption of interferon, the plasma or plasma with leukocytes, is rejoined with the blood cells or formed elements of the blood and returned to the patient.

Suitable techniques for purifying interferon are described in the aforementioned U.S. Pat. Nos. 4,168,261 and 4,172,071. These techniques are also usable with the present invention for removing interferon. It should be appreciated that the techniques in these references will require minor modifications when used in the present invention because the references do not describe the treatment of whole blood or plasma. Suitable sorbents for interferon used with the present invention include anti-interferon globulins against different types of interferon, obtained from animals or by monoclonal antibodies techniques; albumen; and BLUE DEXTRAN 2000

(as described in U.S. Pat. No. 4,172,071). A suitable solid support for these sorbents is SEPHAROSE (as also described in U.S. Pat. No. 4,172,071).

The effectiveness of the present invention when treating autoimmune diseases and hypersensitivity of immediate type could be enhanced when a combined sorbent is used that removes both interferon and autoantibodies from the blood being treated.

One example of treating an autoimmune disease uses a combined sorbent that has a first component that absorbs interferon and a second component, for example, DNA to absorb anti-DNA antibodies. Such combined sorbent is useful when treating blood from patients having systemic lupus erythematosus.

In still another example of treating an autoimmune disease, for example, rheumatic fever, the invention uses a combined sorbent, with a first sorbent being provided for removing interferon and a second sorbent being provided for removing antibodies against cardiac tissue. The second sorbent can include both certain serotypes of streptococcus and antigens of cardiac tissue.

When treating certain diseases connected with hypersensitivity of the immediate type, for instance, bronchial asthma, a combined sorbent having a first component for absorbing interferon and a second component made of an antibody against IgE (immunoglobulin E) is used in the present invention so that both interferon and IgE are removed during treatment of the patient's blood. The invention, and its objects and advantages, will become more apparent in the detailed description of the preferred embodiments hereinafter presented.

BRIEF DESCRIPTION OF THE DRAWINGS

In the detailed description of the preferred embodiments of the invention hereinafter presented, reference is made to the accompanying drawings, in which.

DESCRIPTION OF THE PREFERRED EMBODIMENTS

The present description will be directed in particular to elements forming part of, or cooperating more directly with, the present invention. Elements not specifically shown or described herein are understood to be selectable from those known in the art.

Figure 1:
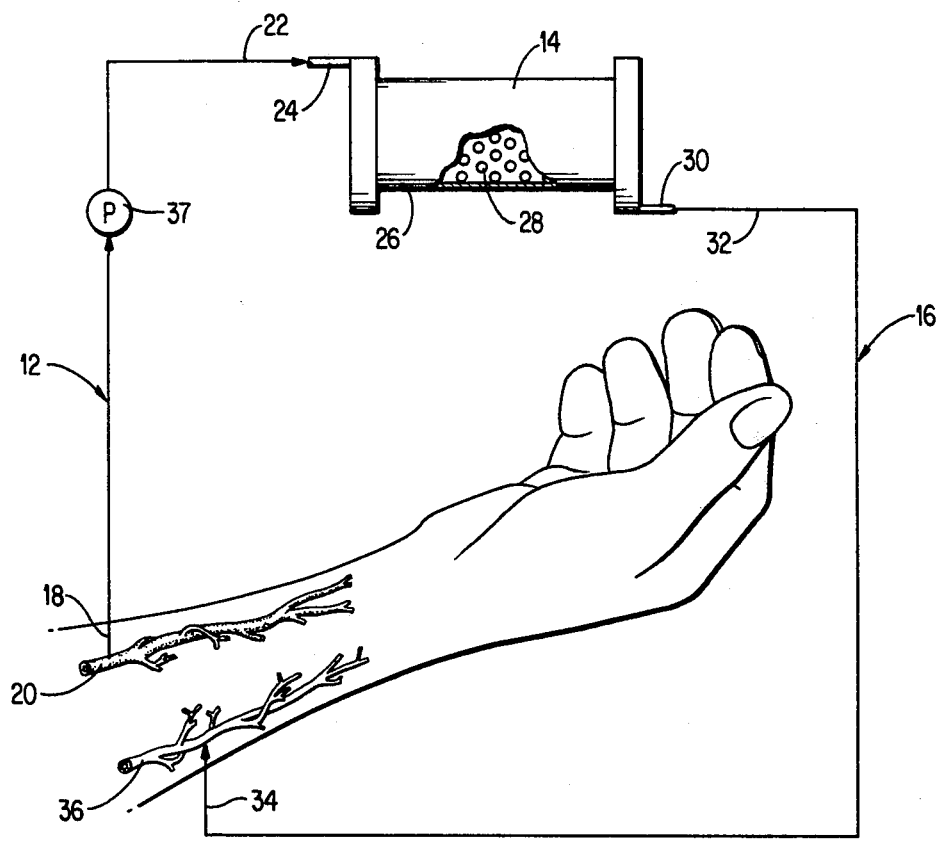
FIG. 1 is a schematic illustration of one embodiment of the present invention.

Referring now to the drawings, and to FIG. 1 in particular, one embodiment of an apparatus for treatment of autoimmune and allergic diseases (hypersensitivity of immediate type) is illustrated. The apparatus, which is generally designated 10, comprises an inlet tube 12, means 14 for removing interferon from blood, and an outlet tube 16. The inlet tube 12 has an inlet end 18 connected to a cannula (not shown) inserted into an artery 20 of a patient. The outlet end 22 of the inlet tube 12 is connected to the inlet 24 of a housing 26 containing a plurality of porous glass beads 28, such as those described in U.S. Pat. No. 4,168,261. The outlet 30 of the housing 26 is connected to an end 32 of the outlet tube 16. The other (outlet) end 34 of tube 16 is connected to a cannula (not shown) inserted into a vein 36 of the patient. Preferably, a pump 37 is included in the apparatus 10. The inlet tube 12 provides means for removing whole blood from a patient, and the outlet tube 16 provides means for returning the blood to the patient. As clearly illustrated in FIG. 1, the tubes 12 and 16 and the means 14 are in continuous fluid communication with each other.

In operation, the cannula connected to the inlet 18 is inserted into an artery of the patient, and the cannula connected to the outlet 34 is inserted into a vein. When a pump is used, the pump is then actuated to pump blood from the patient through the housing 26 so that the beads 28 can remove interferon from the blood. Preferably, all of the interferon is removed from the blood. Blood free from interferon is then returned through the outlet tube 16 into the vein of the patient. Upon completion of the treatment process, the glass beads 28 are removed from the housing 26 and processed to provide interferon for scientific and therapeutic purposes. Thus, the present invention provides a method and apparatus for obtaining interferon for scientific and therapeutic purposes.

The method used with this embodiment of the invention provides a continuous process for treatment of autoimmune and allergic diseases. The process involves removing blood from a patient, passing the removed blood through means for removing interferon from the blood, and returning the blood, which is free from interferon, to the patient.

Figure 2:
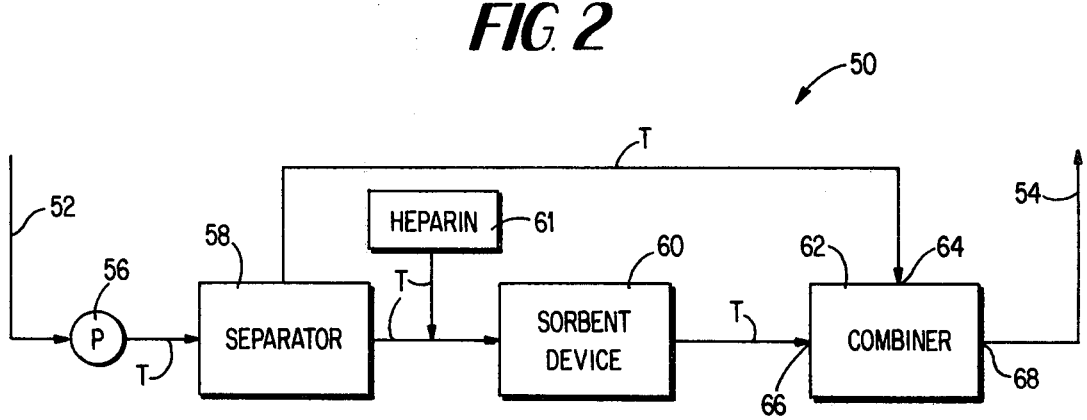
FIG. 2 is a schematic block diagram of another embodiment of the present invention.

Referring now to FIG. 2, another embodiment of an apparatus according to the present invention, generally designated 50, is illustrated. The apparatus 50 includes an inlet tube, generally designated 52, and an outlet tube, generally designated 54. The inlet tube 52 is similar to the inlet tube 12, and the outlet tube 54 is similar to the outlet tube 16 of the embodiment illustrated in FIG. 1. A pump 56 is provided to pump blood from the patient into a separator 58. A suitable separator is a plasma filter of the type described in British Pat. No. 1,562,546. Other suitable methods of plasmapheresis, such as centrifugation, also are usable to separate plasma or plasma with leukocytes from the whole blood. The plasma, or plasma with leukocytes, is fed from the separator 58 to a sorbent containing device 60. Such device can be the means 14 for removing interferon described in connection with FIG. 1, a device using a process of the type described in U.S. Pat. No. 4,172,071, or any other suitable method using a capacious sorbent for interferon carried by a solid support. The plasma, or plasma with leukocytes, after passing through sorbent within the device 60, rejoins the formed elements of blood removed from the whole blood by the separator 58. A combiner 62 is illustrated for providing the mixing function. Such combiner need be no more complex than a mixing valve having one inlet 64 connected to the separator 58 and a second inlet 66 connected to the device 60. The outlet 68 of the valve is connected to the outlet tube 54. A device 61 for adding heparin to the plasma, or plasma with leukocytes, is positionable between the separator 58 and the device 60. Sections of tubing T interconnect the pump 56, the separator 58, the device 60, the device 61, and the combiner 64, as illustrated in FIG. 2. Thus, the various components of the apparatus 50 are in fluid communication with each other.

The method of treating autoimmune and allergic diseases utilizing the apparatus of FIG. 2 involves the connecting of the inlet and outlet tubes to an artery and a vein, respectively, of a patient to be treated; pumping the whole blood of the patient to a separator; separating plasma, or plasma with leukocytes, from blood cells within the separator; passing the plasma, or plasma with leukocytes, through a device for removing interferon;

combining the plasma, or plasma with leukocytes, after absorption of interferon, with the previously removed blood cells; and returning the combined blood to the patient.

In a modification of this embodiment, the separator device separates the blood into plasma (or plasma with leukocytes), lymphocytes (the source of interferon production), and other blood cells. The lymphocytes are discarded and the plasma (or plasma with leukocytes) is processed as previously described.

In another modification, the device 60 utilizes a combined sorbent having a first component for absorbing interferon from the plasma or plasma with leukocytes and a second component that selectively absorbs autoantibodies from the plasma or plasma with leukocytes being treated. The particular component is a function of the disease or condition being treated. By utilizing a combined sorbent, the effectiveness of the invention is enhanced.

Previously, a method and apparatus have been described for the treatment of autoimmune diseases and allergy (hypersensitivity of immediate type). It should be appreciated that the present invention can also be utilized specifically for the purpose of obtaining interferon for therapeutic and scientific purposes. When used in this manner, the first step is to provide healthy donors, which can be either humans or animals. The donors are injected with agents for inducing production of interferon. After the level of interferon in the blood of the donors has reached a desired level, for instance, after approximately six to thirty-six hours, or longer, depending on the type of inducer used, the blood is processed through an apparatus of the type illustrated in either FIG. 1 or FIG. 2. The blood, after being treated in such apparatus, is returned to the donor. With this embodiment, the blood can be removed from either blood vessel, that is, a vein or an artery. The blood, after processing, is then returned to a vein.

Previously, specific embodiments of the present invention have been described. It should be appreciated, however, that these embodiments have been described for the purposes of illustration only, without any intention of limiting the scope of the present invention. Rather, it is the intention that the present invention be limited only by the appended claims.

What is claimed is:

1. A method for treating autoimmune diseases and allergy (hypersensitivity of immediate type) using an apparatus having, in continuous fluid communication, an inlet tube, absorbing means for absorbing and thereby removing interferon from the whole blood, and an outlet tube, said method comprising:
   connecting the inlet tube of said apparatus to a blood vessel of a patient and connecting the outlet tube of said apparatus to a vein of the patient;
   removing blood from the blood vessel of the patient;
   passing the removed blood through the absorbing means for absorbing interferon to thereby reduce the amount of interferon in the blood; and
   returning the blood to the vein of the patient.

2. A method for the treatment of autoimmune diseases and allergy (hypersensitivity of immediate type) utilizing an apparatus having, in fluid communication with each other, an inlet tube, means for separating plasma from whole blood, absorbing means for absorbing and thereby removing interferon from the plasma, and an outlet tube, said method comprising:
   connecting the inlet tube of the apparatus to a blood vessel of a patient and connecting the outlet tube to a vein of the patient;
   removing blood from the blood vessel of the patient;
   separating the removed blood into blood cells and plasma;
   passing the plasma through absorbing means for absorbing interferon from the plasma to thereby reduce the level of interferon within the plasma;
   combining the plasma having a reduced level of interferon with the blood cells previously removed from the blood; and
   returning the combined blood cells and plasma to the vein of the patient.

3. The method according to claim 1, wherein the removed blood is passed through the means for removing interferon to eliminate interferon from the blood.

4. The method according to claim 2, wherein all of the interferon is removed from the plasma.

5. The method according to claim 2, wherein the separating of the removed blood into blood cells and plasma further comprises separating lymphocytes from the blood, the separated lymphocytes being discarded.

6. A method for obtaining interferon from a donor utilizing an apparatus having an inlet tube, means for separating plasma from whole blood, absorbing means for absorbing and thereby removing interferon from the plasma, and an outlet tube, said method comprising:
   injecting a healthy donor with an agent for inducing production of interferon;
   connecting the inlet tube of the apparatus to a blood vessel of the donor and connecting the outlet tube to a vein of the donor;
   removing blood through the inlet tube from the blood vessel of the donor;
   separating the removed blood into blood cells and plasma;
   passing the plasma through absorbing means for absorbing interferon from the plasma to thereby remove interferon from the plasma;
   combining the plasma after passage through the absorbing means with blood cells previously removed from the blood; and
   returning the combined blood cells and plasma to the vein of the donor.

7. A method for the treatment of autoimmune diseases and allergy (hypersensitivity of immediate type) utilizing an apparatus having, in fluid communication with each other, an inlet tube, means for separating plasma with leukocytes from whole blood, absorbing means for absorbing and thereby removing interferon from the plasma with leukocytes, and an outlet tube, said method comprising:
   connecting the inlet tube of the apparatus to a blood vessel of a patient and connecting the outlet tube to a vein of the patient;
   removing blood from the blood vessel of the patient;
   separating the removed blood into a first component containing plasma with leukocytes and a second component containing the remaining blood cells;
   passing the plasma with leukocytes through absorbing means for absorbing interferon from the plasma with leukocytes to thereby reduce the level of interferon within the plasma with leukocytes;
   combining the plasma with leukocytes having a reduced level of interferon with the second component of the blood; and returning the combined blood to the vein of the patient.

8. A method for obtaining interferon from a donor utilizing an apparatus having an inlet tube, absorbing means for absorbing and thereby removing interferon from the blood, and an outlet tube, said method comprising:
    injecting a healthy donor with an agent for inducing production of interferon;
    connecting the inlet tube of the apparatus to a blood vessel of the donor and connecting the outlet tube to a vein of the donor;
    removing blood through the inlet tube from the blood vessel of the donor;
    passing the blood through absorbing means for absorbing interferon from the blood to thereby remove interferon from the blood; and
    returning the blood to the vein of the donor.

9. A method for obtaining interferon from a donor utilizing an apparatus having an inlet tube, means for separating plasma with leukocytes from whole blood, absorbing means for absorbing and thereby removing interferon from the plasma with leukocytes, and an outlet tube, said method comprising:
    injecting a healthy donor with an agent for inducing production of interferon;
    connecting the inlet tube of the apparatus to a blood vessel of the donor and connecting the outlet tube to a vein of the donor;
    removing blood through the inlet tube from the blood vessel of the donor;
    separating the removed blood into a first component containing plasma with leukocytes and a second component containing the remaining blood cells;
    passing the plasma with leukocytes through absorbing means for absorbing interferon from the plasma with leukocytes to thereby remove interferon from the plasma with leukocytes;
    combining the plasma with leukocytes after passage through the absorbing means with the second component of the blood; and
    returning the combined blood to the vein of the donor.

10. A method according to one of claims 1, 2, or 7, wherein said absorbing means comprises a combined sorbent having a first sorbent for absorbing interferon and a second sorbent for absorbing autoantibodies from the material being treated.

11. A method according to one of claims 1, 2, or 7, wherein said absorbing means comprises a combined sorbent having a first sorbent for absorbing interferon and a second sorbent for absorbing antigens from the material being treated.

12. The method according to claim 7, wherein all of the interferon is removed from the plasma with leukocytes.

* * * * *